US008556496B2

(12) United States Patent
Hai et al.

(10) Patent No.: US 8,556,496 B2
(45) Date of Patent: Oct. 15, 2013

(54) STIRRING SYSTEM AND OPERATING METHOD THEREOF

(75) Inventors: Wang Hai, Shenzhen (CN); Yang Lin, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 1017 days.

(21) Appl. No.: 12/610,130

(22) Filed: Oct. 30, 2009

(65) Prior Publication Data

US 2010/0110827 A1    May 6, 2010

(30) Foreign Application Priority Data

Oct. 31, 2008 (CN) .......................... 2008 1 0217190

(51) Int. Cl.
*B01F 7/16* (2006.01)

(52) U.S. Cl.
USPC .......................................... 366/198; 366/199

(58) Field of Classification Search
USPC ............................ 366/199, 198, 207; 422/514
See application file for complete search history.

(56) References Cited

U.S. PATENT DOCUMENTS

| | | | | | |
|---|---|---|---|---|---|
| 1,386,280 | A | * | 8/1921 | Schneider | 366/207 |
| 1,392,875 | A | * | 10/1921 | Morris | 366/207 |
| 1,463,744 | A | * | 7/1923 | Lauterbur | 366/198 |
| 1,473,163 | A | * | 11/1923 | Elmer | 416/121 |
| 1,576,525 | A | * | 3/1926 | Friedrich | 366/286 |
| 1,597,712 | A | * | 8/1926 | Bejar | 366/198 |
| 1,967,891 | A | * | 7/1934 | Lamoreaux | 474/86 |
| 2,065,440 | A | * | 12/1936 | Flaum | 366/198 |
| 2,172,593 | A | * | 9/1939 | Prince | 366/198 |
| 2,218,808 | A | * | 10/1940 | Brotheridge | 366/198 |
| 2,438,574 | A | * | 3/1948 | O'Neill | 366/198 |
| 2,477,764 | A | * | 8/1949 | Myers | 366/198 |
| 2,526,351 | A | * | 10/1950 | Grubelic | 366/198 |
| 2,531,989 | A | * | 11/1950 | Prince et al. | 366/198 |
| 2,699,924 | A | * | 1/1955 | Volkmar | 366/198 |
| 2,774,579 | A | * | 12/1956 | Brown et al. | 366/198 |
| 2,815,194 | A | * | 12/1957 | Seyfried et al. | 366/198 |

(Continued)

FOREIGN PATENT DOCUMENTS

| | | |
|---|---|---|
| CN | 1963527 A | 5/2007 |
| CN | 101135694 A | 3/2008 |
| EP | 1460432 A1 | 9/2004 |
| WO | 2006 132209 A1 | 12/2006 |

OTHER PUBLICATIONS

SIPO Search Report for corresponding Chinese application No. 200810217190.7, 4pages, dated Aug. 13, 2009.

(Continued)

*Primary Examiner* — Tony G Soohoo
(74) *Attorney, Agent, or Firm* — Stoel Rives LLP; Kory D. Christensen

(57) ABSTRACT

Disclosed are an improved stirring system and its operating method. The disclosed system includes at least two stirrers and a drive for driving the at least two stirrers to move between their stirring position and non-stirring position, the drive driving the stirrers to perform a stirring operation for a single purpose at a time. The system employs a single drive to drive a plurality of stirrers, which effectively avoids the disadvantage of redundantly stirring the reaction solutions in the reaction vessel not necessary to be stirred, reduces the risk of cross contamination caused by the stirrers and affecting the results by abnormal change in the absorbance, and makes the test results more accurate.

22 Claims, 5 Drawing Sheets

(56) References Cited

U.S. PATENT DOCUMENTS

| | | | |
|---|---|---|---|
| 2,829,872 A * | 4/1958 | MacDougall | 366/198 |
| 4,046,515 A * | 9/1977 | de Leeuw | 422/514 |
| 4,276,260 A * | 6/1981 | Drbal et al. | 422/510 |
| 4,341,736 A * | 7/1982 | Drbal et al. | 422/509 |
| 4,708,023 A * | 11/1987 | Schneider et al. | 73/863.31 |
| 4,879,917 A * | 11/1989 | Eppelmann et al. | 73/866 |
| 4,924,716 A * | 5/1990 | Schneider | 73/866 |
| 5,076,107 A * | 12/1991 | Timmermans et al. | 73/866 |
| 5,413,770 A * | 5/1995 | Sakaguchi et al. | 422/225 |
| 5,682,001 A * | 10/1997 | Hanson et al. | 73/866 |
| 5,796,016 A * | 8/1998 | Muller | 73/866 |
| 5,807,115 A * | 9/1998 | Hu | 434/272 |
| 5,816,701 A * | 10/1998 | Martin et al. | 366/208 |
| 5,820,824 A * | 10/1998 | Tanaka | 422/510 |
| 6,060,024 A * | 5/2000 | Hutchins et al. | 422/81 |
| 6,652,135 B2 * | 11/2003 | Poitras et al. | 366/198 |
| 2003/0058734 A1 * | 3/2003 | Poitras et al. | 366/198 |
| 2006/0152999 A1 * | 7/2006 | Dunfee et al. | 366/118 |

OTHER PUBLICATIONS

English translation of abstract for Chinese Patent Application No. 1963527 (reference above).

English translation of abstract for Chinese Patent Application No. 101135694 (reference above).

English translation of abstract for WIPO Publication No. 2006/132209 (reference above).

He, Wen-Jun and Chen Jung-Sho, Results and Effects of Stirring Rods at Position R1 and Position S, Journal of Modern Laboratory Medicine vol. 21, No. 2 (2006): pp. 24-25, ISBN 1671-7414, CN 61-1398/R (No English Translation Available).

Chen, Guang and Chen, Shao-Lien, "The Effects of Stirring Rods In Two Biochemical Reactions", Guangzhou Medical Journal vol. 36, No. 6 (2005): pp. 46-47, ISSN 1000-8535, CN44-1199/R (No English Translation Available).

* cited by examiner

STIRRING SYSTEM AND OPERATING METHOD THEREOF

RELATED APPLICATION

The present application claims priority to Chinese Patent Application No. 200810217190.7, titled "Stirring System and Operating Method Thereof", filed on Oct. 31, 2008, which is incorporated herein by reference in its entirety.

FIELD OF THE INVENTION

The present invention relates to an analyzer for analyzing liquids, in particular to a stirring system for stirring reaction solutions in the analyzer and the operating method of the same.

BACKGROUND OF THE INVENTION

In the medical field, a biochemistry analyzer or an immunity analyzer is often used to test and analyze body fluids gathered from organisms. Commonly used test flows are shown in FIG. 1 and FIG. 2: (1) providing a clean and empty reaction vessel; (2) adding a first reagent R1 to the reaction vessel; (3) adding a sample S to the reaction vessel; (4) stirring the reaction solutions in the reaction vessel, which is also referred to as sample stirring. In FIG. 1 only a sample is added, while in FIG. 2 a second reagent still needs to be added, so that the following steps should be further performed: (5) adding a second reagent R2 to the reaction vessel; (6) stirring the reaction solutions in the reaction vessel, which is also referred to as second reagent stirring; and (7) finishing the reaction.

To react to its fullest, the reaction solutions generally need to be stirred homogeneously after reaction solutions with different compositions are added. In this regard, according to different purposes of the stirring or different reaction solutions added before the stirring, stirring during a general test may be divided into sample stirring and second reagent stirring; for some biochemistry analyzers or immunity analyzers, a first reagent stirring operation would also be performed after the first reagent is added.

In the currently known biochemistry analyzers or immunity analyzers, the stirring system and its operating way generally fall within the following cases.

In the first case, the stirring system is configured to include a plurality of independent subsystems based on different types of stirring, each subsystem comprising a drive and a stirrer. This case is subjected to the disadvantages of high cost and low reliability resulting from use of too many components.

In the second case, a single drive and a single stirrer are used to meet different stirring requirements. This case is typically subjected to such factors as low test speed, complicated cross contamination and the like. Therefore, they are generally employed in low-end analyzers.

In the third case, a single stirring system provided with a number of stirrers is used to meet different stirring requirements. Nevertheless, it is known that analyzers operating in this way at present are all subjected to the following defect that two or more types of stirring for different purposes are forcibly performed simultaneously. As shown in FIG. 3, this case allows only two states: (1) two stirrers perform stirring in the reaction vessel at the same time; and (2) two stirrers perform cleaning in the cleaning pool at the same time. Although saving time for stirring, this stirring mode may give birth to additional problems. That is, some tests do not need stirring at a certain moment while other associated tests do need the stirring. A dilemma exists in which case if stirring is not performed for the tests that require stirring, it will prevent the reaction solutions from being mixed uniformly and affect the normal operation of the reaction, thereby resulting in inaccurate test results; on the other hand, stirring performed for the tests that require no stirring will increase the risk of cross contamination, and is likely to cause changes in the absorbance of the reaction solutions, thereby resulting in inaccurate final test results.

SUMMARY OF THE INVENTION

The technical problem underlying the present invention is to provide a stirring system and its operating method that is configured to be a single system and uses a plurality of stirrers, thereby taking both the cost and the test speed into account and reducing improper stirring. To achieve the above objects, the solutions employed according to some embodiments are as follows.

According to the first aspect of some of the embodiments of the present invention, there is provided a stirring system, comprising: at least two stirrers; and a drive for driving the at least two stirrers to move between their stirring position and non-stirring position, and driving the stirrers to perform a stirring operation for a single purpose at a time.

In one embodiment, the at least two stirrers are configured to locate on a same circumference and driven by the drive to rotate along a same circle track; and the stirring position is on the circle track.

In another embodiment, there is provided only one stirring position on the circle track of the stirrers.

In still another embodiment, the stirring system further comprises cleaning pools in a number equal to or larger than that of the stirrers, wherein the positions of the cleaning pools and the stirring position are equally spaced along the circle track of the stirrers; and an included angle between two adjacent stirrers is 360/(N+1), wherein N is the number of the cleaning pools.

According to the second aspect of the embodiments of the present invention, there is provided a stirring system also, comprising: at least two stirrers; and a drive for driving the at least two stirrers to move between their stirring position and non-stirring position; wherein the at least two stirrers are configured to locate on a same circumference and driven by the drive to rotate along a same circle track; and the stirrers have only one stirring position on the circle track.

According to the third aspect of the embodiments of the present invention, there is still provided a stirring system, comprising: at least two stirrers; at least one cleaning pool; and a drive for driving the at least two stirrers to move between their stirring position and non-stirring position; wherein the positions of the at least one cleaning pool and the stirring position are equally spaced along a same circle track; the drive drives the at least two stirrers to rotate along the circle track; and the stirrers perform a stirring operation for a single purpose at a time.

According to the fourth aspect of the embodiments of the present invention, there is provided an operating method for a stirring system, comprising the steps: setting a drive and at least two stirrers; and driving the stirrers by the drive to perform only a stirring operation for a single purpose at a time.

In one embodiment, the at least two stirrers are configured to locate on a same circumference and driven by the drive to rotate along a same circle track; and a stirring position is on a circle track.

In another embodiment, the operating method further comprises: arranging cleaning pools in a number equal to or larger than that of the stirrers; and spacing positions of the cleaning pools and stirring positions equally along the circle track of the stirrers; wherein an included angle between two adjacent stirrers is 360/(N+1), where N is the number of the cleaning pools.

The features and advantages of the present invention are described in detail as follows by way of embodiments as illustrated in the accompanying drawings.

DETAILED DESCRIPTION

The present embodiment employs a single stirring system which comprises only one drive and is provided with two or more stirrers as necessary. The drive drives the stirrers to perform a stirring operation for a single purpose at a time, such as sample stirring or second reagent stirring, or other stirring operations. Thus, whatever the test order is, there are no redundant stirring and improper stirring.

Figure 4:
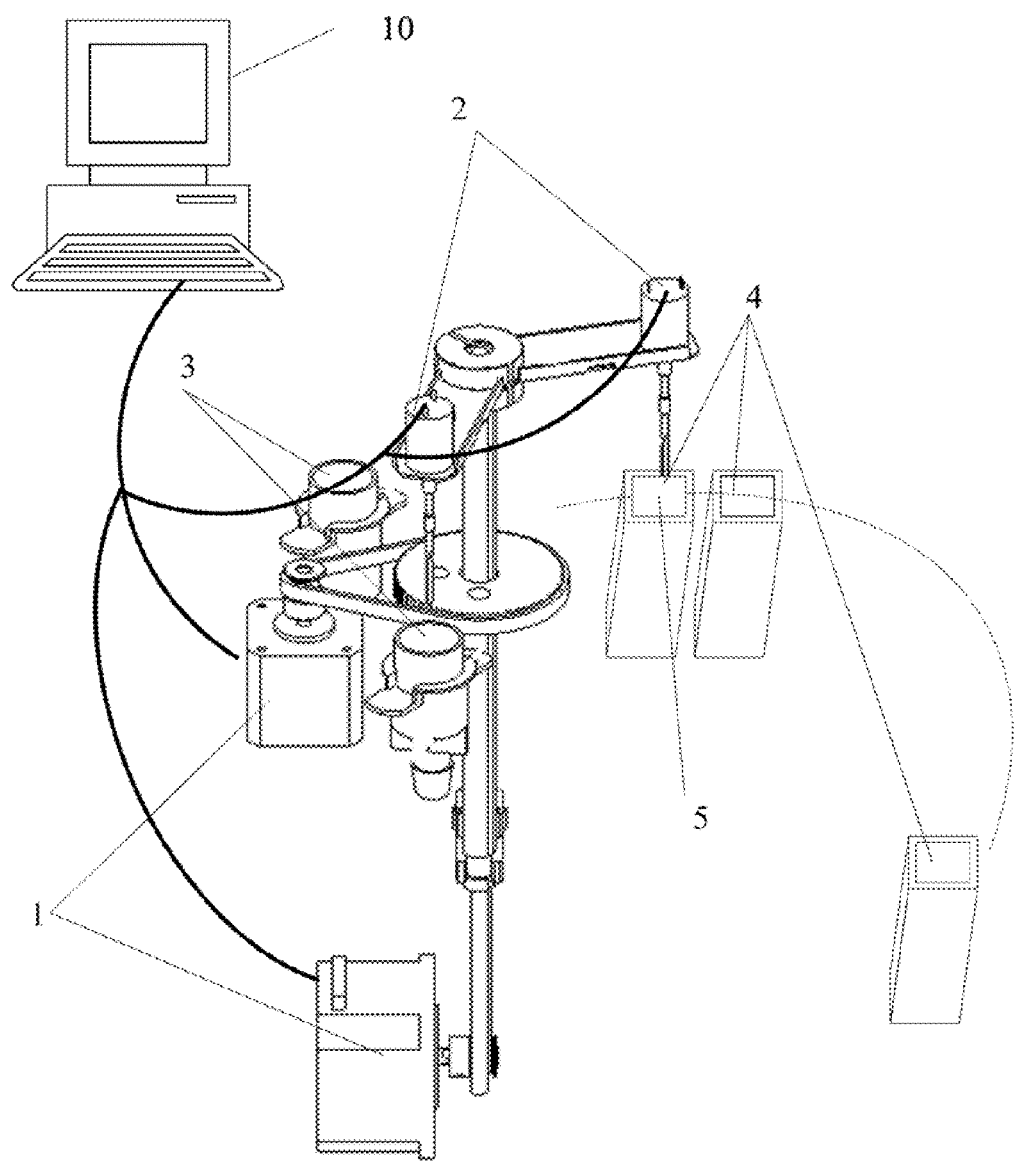
FIG. 4 is a structural schematic diagram of a stirring system according to an embodiment of the present invention.

Referring to FIG. 4, in an embodiment, the stirring system comprises a drive 1, two stirrers 2 and two cleaning pools 3. It may further comprise a controller 10 for scheduling control of the stirrers 2 and the drive 1 based on the requirements of the instrument test flow, so as to accomplish the cooperation for multiple test purposes.

Under the control of the controller 10, the drive 1 performs the function of driving the stirrers 2 to move between their stirring positions and the non-stirring positions. Typically, there are, but not limited to, two driving approaches, i.e., up-and-down movement driving and rotational movement driving. In the context, a particular state into which the drive drives the stirrers is referred to as an operating position. For example, a stirring operating position is a state in which the stirrer is controlled to stir the reaction solutions in the reaction cup in the stirring position; a cleaning operating position is a state in which the stirrer is controlled to clean in a cleaning pool in the cleaning position; and a standby operating position is a state in which the stirring system does not perform any operation and is in a waiting state, wherein both the cleaning operating position and the standby operating position may be called the non-stirring position. A stirring system comprises at least the two cases of a stirring operating position and a non-stirring operating position. A particular position is typically configured for a stirrer for the stirring operation, and is called a stirring position. When in the cleaning operating position and the standby operating position, the stirrer is often in a non-stirring position.

The stirrer 2 stirs and uniformly mixes the reaction solutions in the reaction vessel based on some particular stirring principles. When driven by the drive 1 into the stirring position 5, the stirrer 2 performs the stirring operation; when driven by the drive into a non-stirring position, the stirrer generally performs the cleaning operation or stays in the standby state. In this embodiment, two separate stirrers are provided to perform stirring operations respectively. At the time when the stirring is performed, the stirrer performs the stirring operation on the reaction solutions in the reaction vessel 4 in the stirring position 5.

In order to avoid cross contamination caused by the stirrers, the stirrers generally need a cleaning operation at the conclusion of the stirring operation. This function is performed in the cleaning pool 3. Two cleaning pools are configured in this embodiment.

In an embodiment, two cleaning pools and stirring positions are spaced equally on the same circle track. Driven by the drive 1, the two stirrers 2 may stand above and rotate along the circle track. When a reaction cup is moved to the stirring position, the drive 1 drives one of the stirrers to rotate to the stirring position, move down into the reaction cup to stir the reaction solutions, and perform a stirring operation for a single purpose at a time. That is, only one stirrer performs the stirring operation, conducting sample stirring or second reagent stirring at a time, while other stirrers are in the non-stirring position. When the drive 1 drives one of the stirrers to rotate to a position where a cleaning pool is located, the stirrer performs the cleaning operation.

For the convenience of control, a stirring position is preferably arranged on the rotation circle track of the stirrer. That is, the rotation track of the reaction cup and the rotation circle track of the stirrer intersect at only one point, such that the stirrer stirs in the same stirring position.

In some embodiments, there may be a number of, e.g. two or three, stirring positions along the rotation circle track of the stirrer. In this way, the stirrers may perform the stirring operation in different positions, but only one stirrer performs the stirring operation, i.e. sample stirring or second reagent stirring, at a time as well.

To enable the stirrer to perform the cleaning operation at the stirring time, the included angle between two adjacent stirrers is set to 120 degree. When the stirrers stop on the circle track, each stirrer stands either in a cleaning pool or in a stirring position. It is noted, however, that some embodiments may be implemented where the stirrers are set in different positions and angles from that shown in the illustrated embodiment, so long as the cleaning pools and stirring positions corresponding spaced to match the correct positions and angles of the stirrers.

In other embodiments, the stirring system comprises a drive and at least two stirrers, and in some embodiments may further comprise at least one cleaning pool, for example, two stirrers and one cleaning pool, or three stirrers and four cleaning pools. The stirrers are arranged to locate on the same circumference and driven by the drive to rotate along the same circle track, and the positions of the cleaning pools and the stirring positions are equally spaced along the rotation circle track of the stirrers, such that the stirrers driven by the drive only perform the stirring operation for a single purpose at a time, i.e., one stirrer performs sample stirring or second reagent stirring or other stirring operations, while other stirrers are in the non-stirring positions. It depends on the real-time requirements of the instrument to determine which stirring to be particularly performed.

In order to enable the stirrers in the non-stirring positions to perform the cleaning operation at the stirring time, the included angle between two adjacent stirrers is set to 360/(N+1), where N is the number of the cleaning pools. In this way, when one of the stirrers is in the stirring position, the other stirrers may at least partly stand in the cleaning pool positions to perform cleaning Preferably, the number of the stirrers is less than or equal to the number of the cleaning pools, such that when one of the stirrers performs the stirring operation, all of the other stirrers are in the cleaning pools, making it unnecessary to specially assign a cleaning time and thus improving the test speed.

In the standby state, the stirrers may be controlled to stand in the cleaning pools.

For a system provided with two rings of reaction cups (i.e. an inner ring and an outer ring) on the reaction disk, the stirrers in the stirring system may also be designed to be connected with each other in parallel; that is, two stirrers are arranged on the same radial line, and are bound together and driven by the drive to perform the same movement, corresponding respectively to the inner and outer rings of reaction cups at the same positions (i.e. at the same radial line) on the reaction disk. Since the inner and outer rings of reaction cups at the same position require the same stirring operation, the stirrers connected with each other in parallel perform the same stirring operation as well, i.e., the stirring operation for a single purpose.

Figure 5:
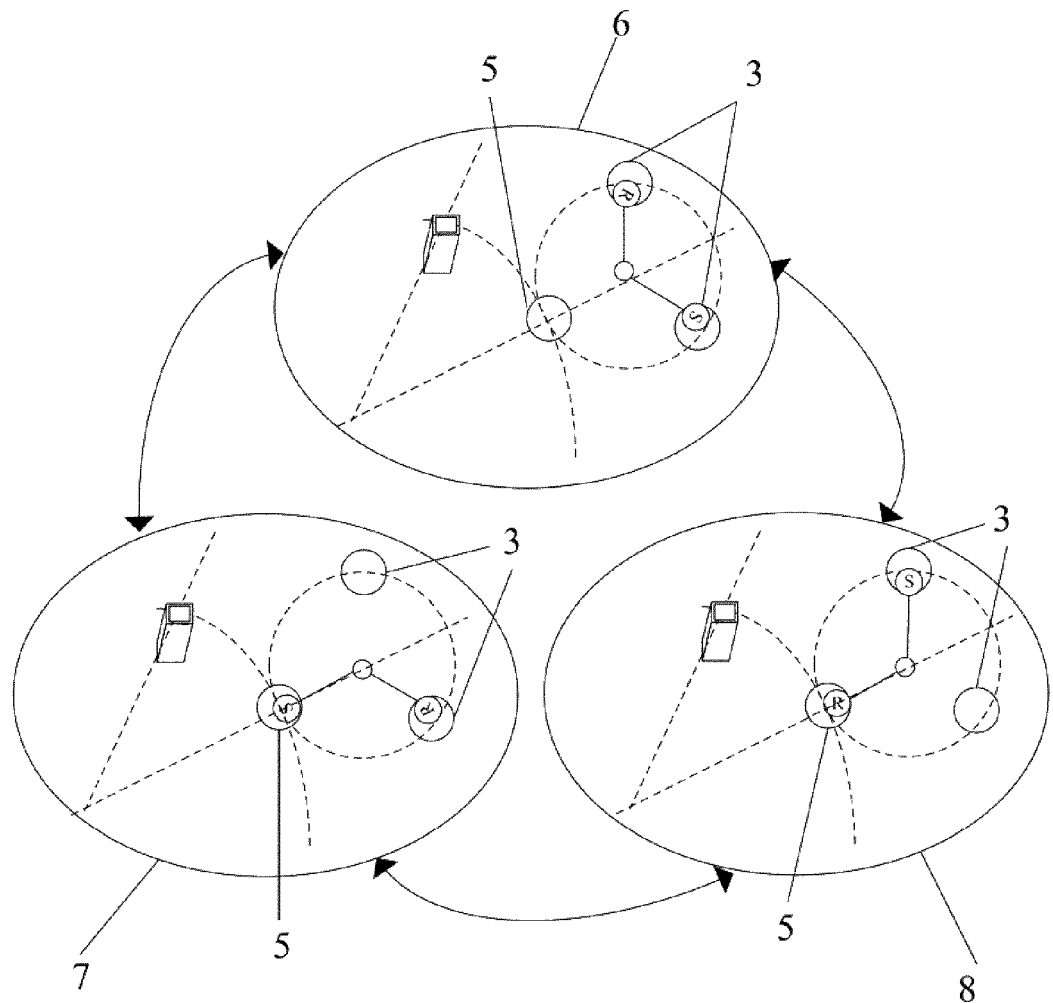
FIG. 5 is an operating position state transition diagram according to an embodiment of the present invention.

The operating position state transition is described below with two stirrers and two cleaning pools as an example, as can be seen from the operating position state transition diagram shown in FIG. 5.

The stirring system, in the case of standby, is in the standby operating position 6, while the two stirrers marked by R\S in the figure are in the cleaning pools 3 respectively. Therefore, this state may also be referred to as the cleaning operating position.

When the sample stirring needs to be performed for the reaction vessel in the stirring position, the system comes into the sample stirring operating position 7, and controls the drive to rotate the stirrers. Then the stirrer marked as S comes into the stirring position 5 and performs the sample stirring in the reaction vessel in the stirring position, and the other stirrer marked as R comes into the cleaning pool 3.

When the second reagent stirring needs to be performed for the reaction vessel in the stirring position, the system comes into the second reagent stirring operating position 8. Then the stirrer marked as R comes into the stirring position 5, and the other stirrer marked as S comes into the cleaning pool 3.

As seen from above, in the sample stirring operating position 7, the stirrer marked as R would be in the cleaning pool at the same time, and thus may also be cleaned at this time; and in the second reagent stirring operating position 8, the stirrer marked as S would also be in the cleaning pool at the same time, and may be cleaned then, which can both save the time for the operation of the system and improve the cleaning effect of the stirrers.

In summary, the system according to the embodiment employs a single drive to drive a plurality of stirrers, which effectively avoids the disadvantage of redundantly stirring the reaction solutions in the reaction vessel not necessary to be stirred, reduces the risk of cross contamination caused by the stirrers and affecting the results by abnormal change in the absorbance, and makes the test results more accurate.

Figure 1:
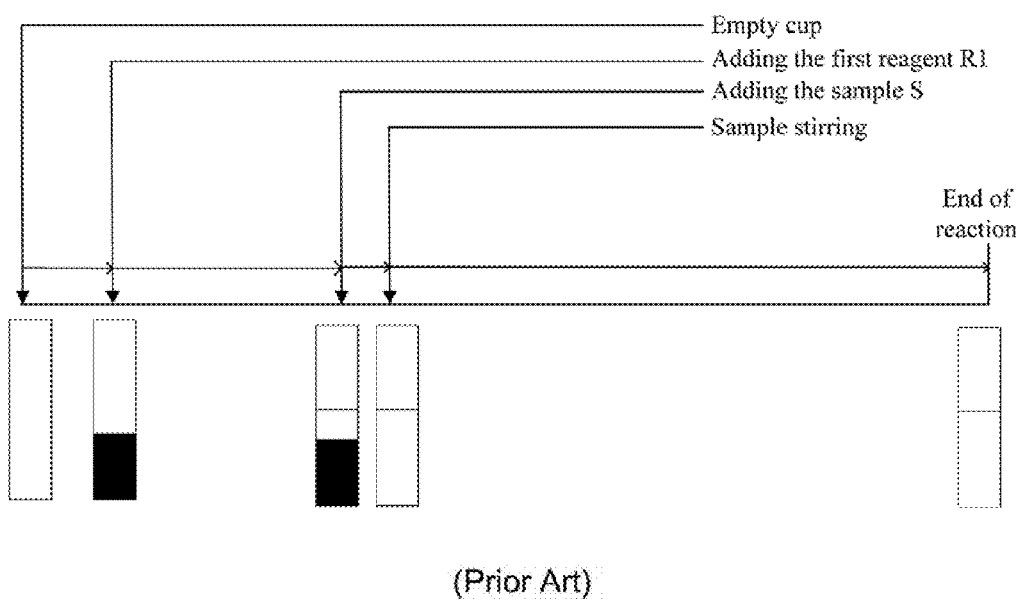
FIG. 1 is a flow diagram of a single reagent project test.
Figure 2:
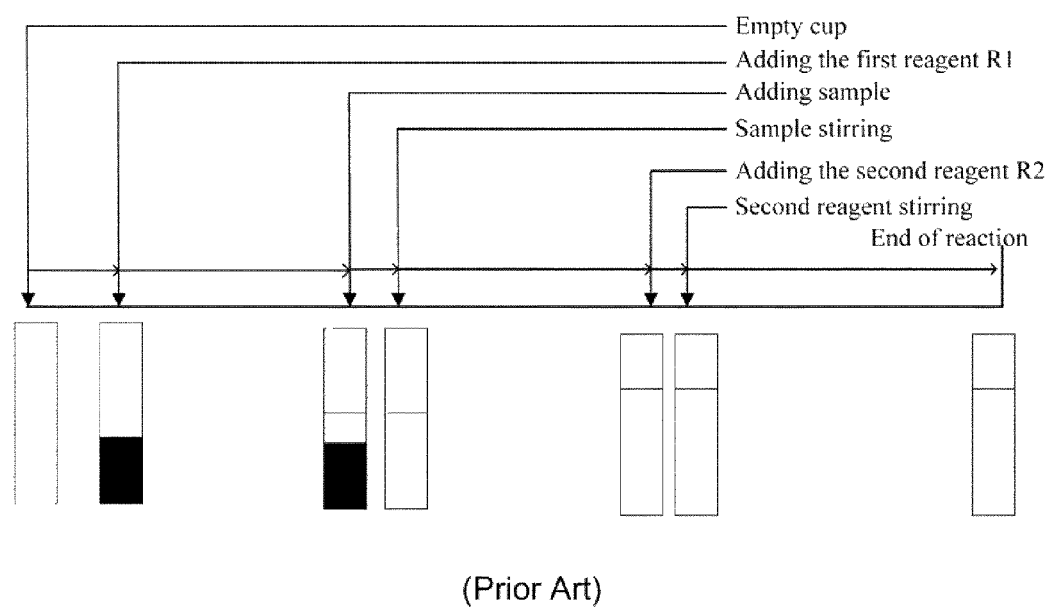
FIG. 2 is a flow diagram of a dual reagent project test.
Figure 3:
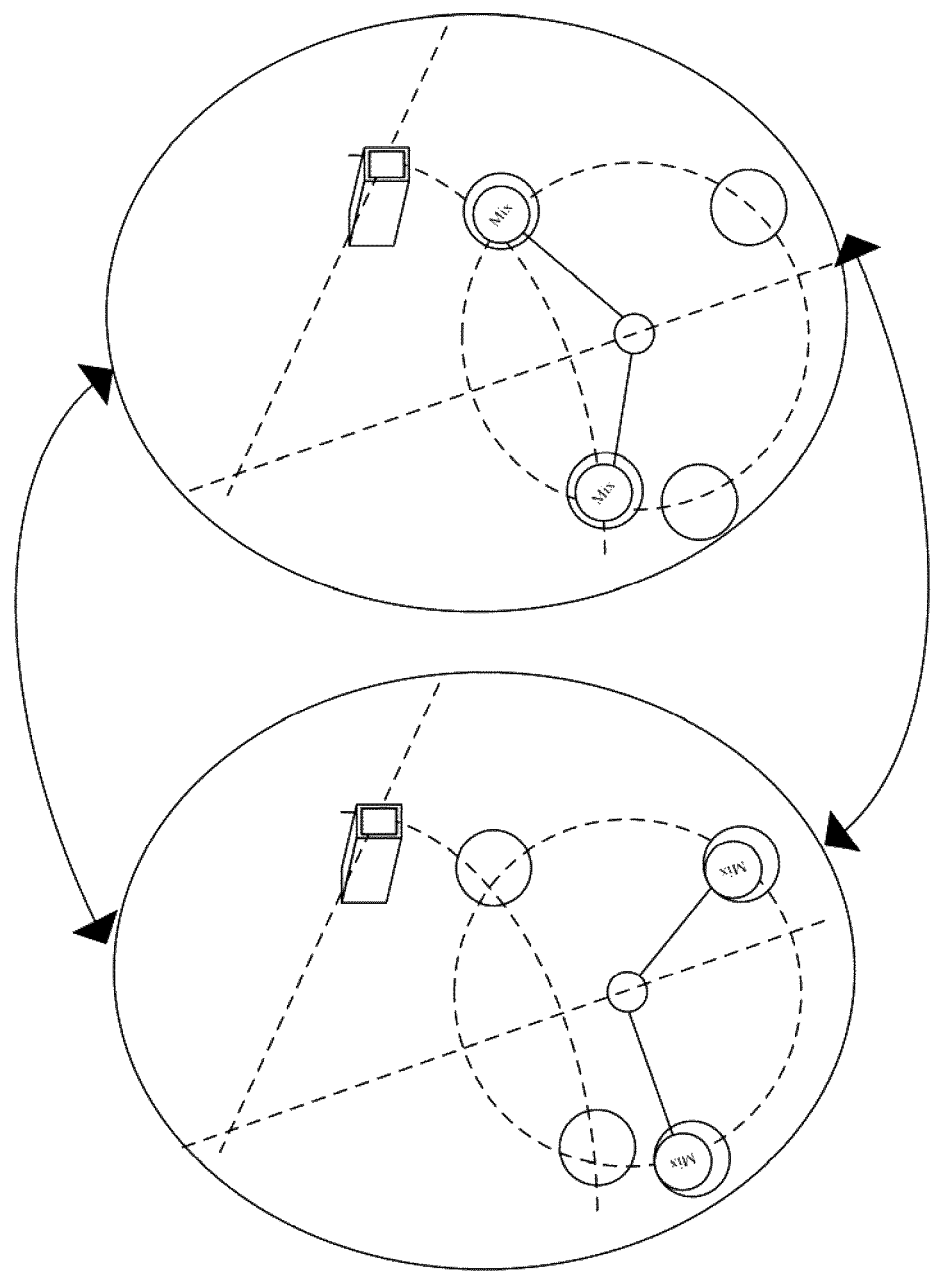
FIG. 3 is an operating position state transition diagram in the prior art.

The system according to the embodiment is adapted to the stirring for a single purpose, i.e., the sample stirring as shown in FIG. 1. Meanwhile, it is also adapted to the stirring for two purposes, i.e., the sample stirring and the second reagent stirring as shown in FIG. 2.

The foregoing is a more detailed description of the system according to the present invention by preferred embodiments. However, the present invention is not limited to those specific embodiments. It will be appreciated by those skilled in the art that several simple inferences or substitutions may be made without departing from the concept of the present invention, which should be considered within the protection scope of the present invention.

The invention claimed is:

1. A stirring system, comprising:
   at least two stirrers; and
   a drive for driving the at least two stirrers to move between a stirring position of one or more stirring positions and a non-stirring position of one or more non-stirring positions, and to drive the at least one stirrer of the at least two stirrers to perform a same stirring operation for a single purpose at a time, wherein
   the at least two stirrers are arranged on a same circumference and driven by the drive to rotate along a same circular track segment, and
   the stirring position is located on the same circular track segment.

2. The stirring system according to claim 1, wherein there is provided only one stirring position on the same circular track segment for each of the at least two stirrers.

3. The stirring system according to claim 1, further comprising:
   a first number of cleaning pools, wherein
   the first number is equal to or larger than a total number of the at least two stirrers,
   positions of the cleaning pools and the stirring position are equally spaced along the same circular track segment of the at least two stirrers, and
   centers of two adjacent stirrers and a center of the same circular track segment form an angle of 360/(N+1) degrees, wherein N denotes the first number of the cleaning pools.

4. The stirring system according to claim 1, wherein the drive actuates one or more but not all of the at least two stirrers to perform the same stirring operation.

5. The stirring system of claim 1, further comprising:
   a plurality of reaction cups that are arranged along a circular path segment, in which the circular path segment intersects the circular track segment of the at least two stirrers at only one point.

6. The stirring system of claim 1, wherein the drive actuates a first stirrer of the at least two stirrers to the stirring position to perform the same stirring operation while a second stirrer of the at least two stirrers is actuated by the drive to the non-stirring position for receiving a cleaning operation.

7. The stirring system of claim 6, wherein no separate time period is allocated for cleaning the second stirrer during an operation cycle in which one stirring operation is initiated and completed.

8. The stirring system of claim 1, further comprising:
   a total number of non-stirring positions in which at least some of the at least two stirrers are not performing the same stirring operation, wherein the total number of the non-stirring positions is greater than or equal to a maximum number of concurrent stirring positions in which one or more stirring operations occur concurrently.

9. The stirring system of claim 1, wherein the drive is configured to actuate a first stirrer and a second stirrer of the at least two stirrers to perform identical functions such that when the first stirrer performs a first function at a time point, the second stirrer is also actuated to perform the first function at the time point.

10. A stirring system, comprising:
    at least two stirrers;
    a drive to drive the at least two stirrers to move between a stirring position and a non-stirring position, wherein
    the at least two stirrers are arranged on a same circumference and driven by the drive to rotate along a same circular track segment, and the stirring position of the at least two stirrers contains only one position on the same circular track segment.

11. The stirring system according to claim 10, further comprising:
a first number of cleaning pools, wherein the first number is equal to or larger than a second number of the at least two stirrers, positions of the cleaning pools and the stirring position are equally spaced along the circular track segment of the at least two stirrers, and centers of two adjacent stirrers and a center of the circular track segment form an angle of 360/(N+1) degrees, where N denotes the first number of the cleaning pools.

12. A stirring system, comprising:
at least two stirrers;
at least one cleaning pool; and
a drive for driving the at least two stirrers to move between a stirring position and a non-stirring position of the at least two stirrers, wherein
a cleaning pool position of the at least one cleaning pool and the stirring position are equally spaced along a same circular track segment,
the drive drives the at least two stirrers to rotate along the same circular track segment, and
the at least two stirrers perform a same stirring operation for a single purpose at a time.

13. The stirring system according to claim 12, wherein the stirring position contains only one position for the at least two stirrers to perform the same operation along the circular track segment.

14. The stirring system according to claim 12, wherein centers of two stirrers that are adjacent to each other and a center of the circular track segment form an angle of 360/(N+1) degrees, where N denotes a first total number of the at least one cleaning pool, and a second total number of the at least two stirrers is less than or equal to the first total number of the at least one cleaning pool.

15. A stirring system, comprising:
at least two stirrers that are both driven by a same drive mechanism, wherein
the at least two stirrers are spaced apart such that fewer than all of the at least two stirrers perform a same stirring operation at a given time, and
the at least two stirrers are driven by the same drive mechanism to rotate along a same circular track segment, and
a stirring position for the same stirring operation is located on the same circular track segment.

16. The stirring system according to claim 15, wherein the at least two stirrers correspond to one or more specific stirring positions on the circular track segment.

17. The stirring system according to claim 15, further comprising:
a first total number of cleaning pools, wherein
the first total number is equal to or larger than a second total number of the at least two stirrers, and
positions of the first total number of the cleaning pools and the stirring positions are equally spaced along the circular track segment.

18. The stirring system according to claim 17, in which centers of two adjacent stirrers of the at least two stirrers and a center of the circular track segment form an angle of 360/(N+1) degrees, wherein N denotes the first total number of the cleaning pools.

19. The stirring system according to claim 15, wherein the same drive is configured to drive one or more but not all of the at least two stirrers to stir a sample or to stir a reagent at a time.

20. A stirring system, comprising:
a single drive mechanism; and
at least two stirrers that are both driven by the single drive mechanism, wherein
the at least two stirrers are spaced apart from each other such that fewer than all of the at least two stirrers perform a same stirring operation at a given time,
the at least two stirrers are driven by the single drive mechanism to jointly rotate along at least two curved track segments to traverse between stirring positions and non-stirring positions, and
the stirring positions and the non-stirring positions are located on the at least two curved track segments.

21. The stirring system of claim 20, wherein the at least two curved track segments are concentric.

22. The stirring system of claim 20, wherein the drive actuates a first stirrer and a second stirrer of the at least two stirrers together to enter their respective reaction cups concurrently.

* * * * *